(12) United States Patent
Laskey et al.

(10) Patent No.: US 6,521,405 B1
(45) Date of Patent: Feb. 18, 2003

(54) CELL-FREE REPLICATION SYSTEM AND USES THEREOF

(75) Inventors: Ronald Laskey; Gareth Haydn Williams; Torsten Krude; Kal Stoeber; Anthony David Mills, all of Cambridge (GB)

(73) Assignee: Cancer Research Campaign Technology Limited, London (GB)

( * ) Notice: Subject to any disclaimer, the term of this patent is extended or adjusted under 35 U.S.C. 154(b) by 0 days.

(21) Appl. No.: 09/486,610

(22) PCT Filed: Sep. 2, 1998

(86) PCT No.: PCT/GB98/02634

§ 371 (c)(1), (2), (4) Date: Mar. 9, 2000

(87) PCT Pub. No.: WO99/11776

PCT Pub. Date: Mar. 11, 1999

(30) Foreign Application Priority Data

Sep. 2, 1997  (GB) ............................................... 9718624
Jun. 15, 1998 (GB) ............................................... 9812886

(51) Int. Cl.[7] ........................... C12Q 1/68; C12P 19/34; C12N 1/38; C12N 5/00
(52) U.S. Cl. ........................ 435/6; 435/91.1; 435/243; 435/244; 435/420
(58) Field of Search ................. 435/6, 91.1, 420, 435/244, 243

(56) References Cited

U.S. PATENT DOCUMENTS 6,107,042 A * 8/2000 Laskey et al. ................. 435/6

FOREIGN PATENT DOCUMENTS

GB  WO-97/49797 A1 * 12/1997
WO  WO 97/49797       12/1997

OTHER PUBLICATIONS

Leno et al. "Initiation of DNA replicationin Nuclei from Quiescent Cells Requires Permeabilization of the Nuclear Membrane" Journal of Cell Biology, 1994, 127(1):5–14.*
Academic Press Dictionary of Science and Technology, C. Morris, ed. Academic Press, 1992, p. 2054.*
Krude et al., "Cyclin/Cdk–Dependent Initiation of DNA Replication in a Human Cell–Free System", Cell, vol. 88, 109–119, Jan. 10, 1997.
Otaegui et al., "Transfer of Nuclei From 9–Cell Stage Mouse Embryos Following Use of Nocodazole to Control the Cell Cycle", Molecular Reproduction and Development, vol. 39, No. 2, pp. 147–152, Oct. 1994.
Derwent (Database WPI); AN 98–191873; RU 2 088 661 C, Aug. 27, 1997 (Saksess Stock Co).
Sanders Williams et al., "A Human Protein Related to Yeast Cdc6p", Proc. Natl. Acad. Sci. USA, vol. 94, No. 1 pp. 142–147, Jan. 1997.
Wilmut et al., "Viable Offspring Derived From Fetal and Adult Mammalian Cells", Nature, vol. 385, No. 6619, pp. 810–813, Feb. 27, 1997.
Campbell et al., "Sheep Cloned by Nuclear Transfer From a Cultured Cell Line", Nature, vol. 380, No. 6569, pp. 64–66, Mar. 7, 1996.

(List continued on next page.)

*Primary Examiner*—W. Gary Jones
*Assistant Examiner*—B J Forman
(74) *Attorney, Agent, or Firm*—Nixon & Vanderhye P.C.

(57) ABSTRACT

The invention relates to improvements in cell-free systems for initiating DNA replication under cell cycle control. The system comprises a synchronous population of G1 nuclei which have been released from G0; and S phase cytosol. In a preferred aspect, a polypeptide is supplied to the system, wherein the polypeptide is Cdc6 and/or at least one MCM protein. The system is suitable for DNA replication assays, for example to test substances which modulate DNA replication.

11 Claims, 3 Drawing Sheets

OTHER PUBLICATIONS

Coleman et al., "The Xenopus Cdc6 Protein is Essential for the Initiation of a Single Round of DNA Replication in Cell–Free Extracts", Cell, vol. 87, No. 1, pp. 53–63, Oct. 4, 1996.

Stillman, B, "Cell Cycle Control of DNA Replication", Science, vol. 274, pp. 1659–1663, Dec. 6, 1996.

"Nuclear DNA Synthesis In Vitro Is Mediated via Stable Replication Forks Assembled in a Temporally Specific Fashion In Vivo" Nicholas H. Heintz and Bruce W. Stillman, Dpt. of Pachology, University of Vermont College of Medicine, Burlington, Vermont 05405, and Cold Spring Harbor Laboratory. Cold Spring Harbor, New York 11724 Molecular and Cellular Biology, May 1988 P. 1923–1931, American Society for Microbiology.

* cited by examiner

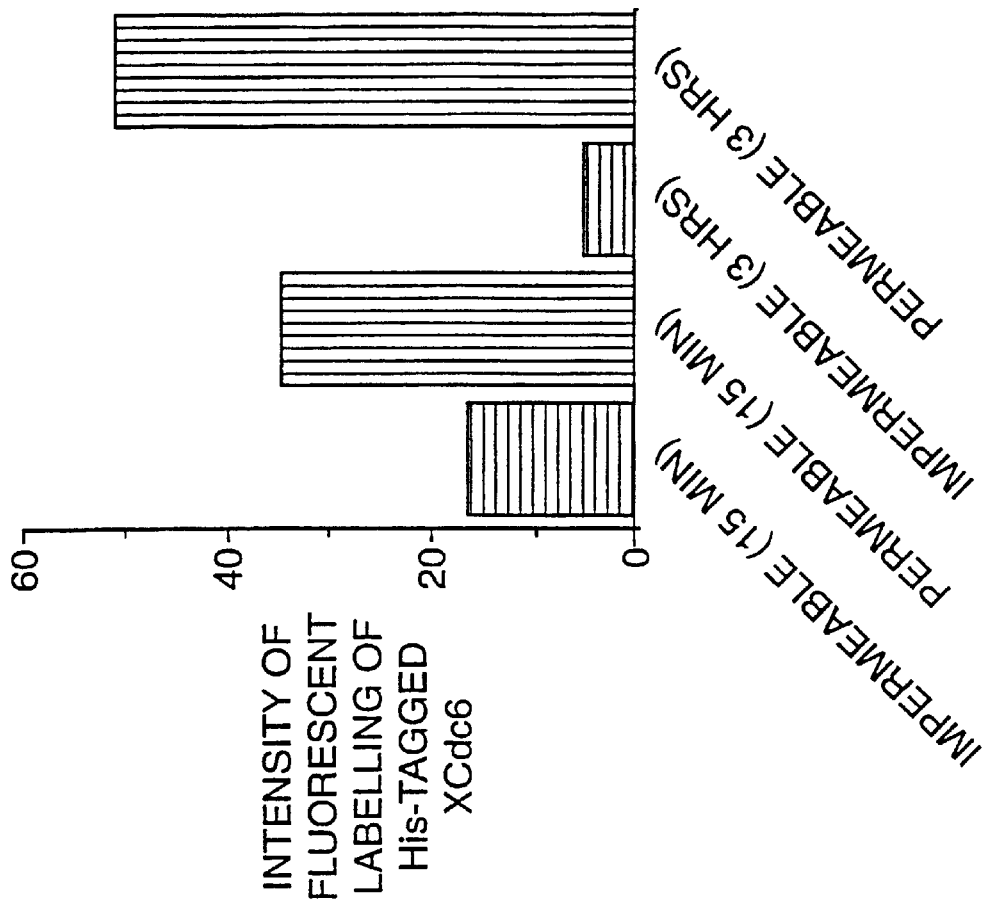
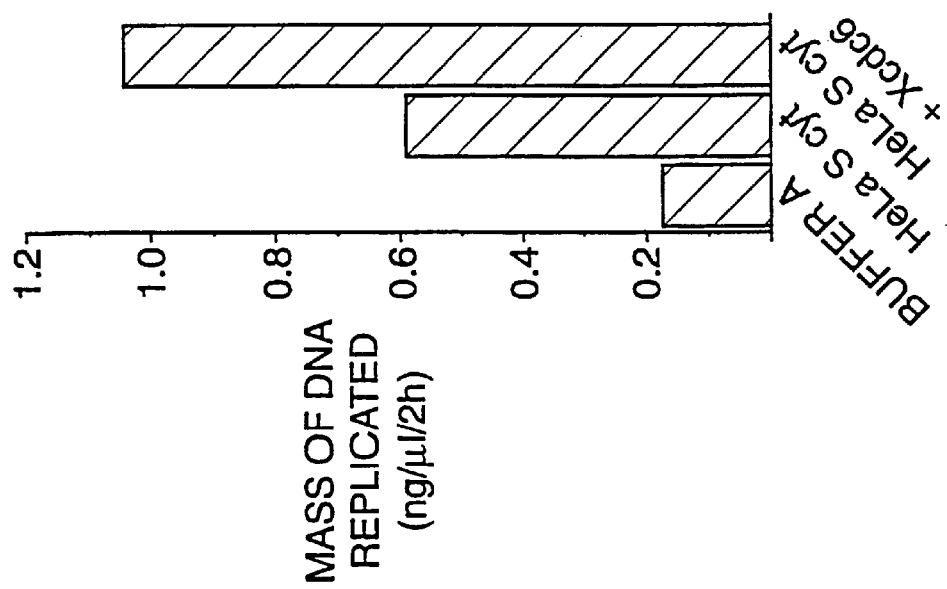

CELL-FREE REPLICATION SYSTEM AND USES THEREOF

This application is a 371 of PCT/Gb98/02634, filed Sep. 2, 1998.

The present invention relates to in vitro procedures for DNA replication, and more particularly provides a system for initiating semi-conservative DNA replication under somatic cell cycle control. It also relates to induction of premature competence to replicate. It also relates to the use of such a system, for example in identifying agents that modulate DNA replication, in particular inhibit or stimulate it, thereby providing for example agents having utility based on therapeutic potential.

BACKGROUND OF THE INVENTION

The mechanisms which regulate the eukaryotic cell cycle are complex and the subject of much research. There is a continuing need for the development of good model systems which allow investigation of the mechanisms of action of particular components of the cell cycle under controlled conditions to provide insights into the control of DNA replication and its coupling to the cell cycle in eukaryotic, particularly human, cells. In addition, such systems will allow a range of uses in deriving products of practical benefit, such as screening and identifying therapeutic agents which inhibit DNA replication, and which could thus be used as anti-cancer drugs, and also agents which stimulate DNA replication, which could be used for tissue repair therapeutics.

An important aspect of a good model system is one in which a population of cells, or cellular nuclei, are synchronized with respect to the cell cycle. In proliferating cells, the cell cycle can be divided into four main stages. Following the production of a new cell by mitotic division, there is a period of time, G1, prior to the start of DNA synthesis in the S phase. During the S phase the genome of the cell is replicated and this is followed by an interval, G2, prior to mitosis (the M phase). Following mitosis, the cells reenter the G1 phase. Non-replicating cells generally exit the cell cycle during G1 into the G0 phase.

The initiation of DNA replication, i.e. the transition from G1 to S, is a key step in the regulation of the cell division cycle. A plethora of intra-and extracellular signals is integrated during G1 phase of the cell cycle into a decision to withdraw from the division cycle, or to initiate S phase and hence to continue proliferation (Heichman and Roberts, 1994). Once S phase is initiated, control mechanisms ensure that all chromosomal DNA is replicated before chromosomes are segregated into the two daughter cells at mitosis (Nurse, 1994).

Cell fusion and nuclear transplantation experiments provided compelling evidence that quiescent cell nuclei are induced to initiate DNA replication when introduced into S phase cells (Graham et al., 1966; Harris et al., 1966; de Terra, 1967; Johnson and Harris, 1969). When synchronized cells were fused, S phase cells induced DNA replication only in G1 nuclei, but not in G2 nuclei (Harris et al., 1966; de Terra, 1967; Guttes and Guttes, 1968; Ord, 1969; Rao and Johnson, 1970). These results indicated that S phase cells contain dominant specific factors that trigger DNA replication and are evolutionarily conserved. Unreplicated G1 nuclei are the physiological substrates for the initiation of DNA replication, whilst re-replication in G2 nuclei is prevented until they have undergone mitosis (Romanowski and Madine, 1996).

The transition from G1 to S is regulated by a number of proteins within the cell, in particular the cyclins A, D and E, and their associated cyclin-dependent kinases (Cdks), particularly Cdk2.

One of the major mechanisms by which a replication-competent state during the G1 phase of the cell cycle is achieved involves the regulated assembly of pre-replicative complexes (pre-RCs) or "replication licences" at origins of replication during G1 (Diffley et al., 1994, reviewed by Donovan and Diffley, 1996).

The pre-RC includes two heteromeric protein complexes, the minichromosome maintenance complex (MCM) and the origin recognition complex (ORC), together with the monomeric protein Cdc6 (reviewed by Dutta and Bell, 1997,; Newlon, 1997; Romanowski and Madine, 1997).

The six-subunit origin-recognition complex (ORC) binds specifically to S. cerevisiae autonomously replicating sequences (ARS) throughout the cell cycle (Bell and Stillman, 1992; Diffley and Cocker 1992; Aparicio et al., 1997; Liang and Stillman, 1997; Tanaka et al., 1997). Although origins of replication have been difficult to define in higher eukaryotes, homologues of the yeast ORC proteins have a similar function in that they are required for initiation of replication (Gavin et al., 1995; Carpenter et al., 1996; Coleman et al., 1996; Romanowski et al., 1996a; Rowles et al., 1996).

In yeast, it has been shown that the monomeric Cdc6 protein is essential for the initiation of DNA replication and is required for the assembly and maintenance of the pre-Rc (Kelly et al., 1993; Liang et al., 1995; Nishitani and Nurse, 1995; Piatti et al., 1995; Cocker et al., 1996; Muzi-Falconi et al., 1996; Detweiler and Li, 1997, 1998) but its role in mammalian cells is less well characterised (Yan et al., 1998).

The six members of the MCM protein family (MCM2-7) are also components of the pre-RC and association of these proteins with chromatin is required for initiation of DNA replication (Chong et is al., 1995; Dalton and Whitbread, 1995; Kubota et al., 1995; Madine et al., 1995a). During replication the MCM proteins become phosphorylated and displaced from chromatin (Kimura et al., 1994;Chong et al., 1995; Kubota et al., 1995; Madine et al., 1995a, 1995b; Todorov et al., 1995; Coué et al., 1996; Hendrickson et al., 1996; Krude et al., 1996). Cells arrested in vitro by serum starvation or contact inhibition lose chromatin-bound MCMs (after a few days). Although the total level of MCMs in the cells does not decrease greatly within 14 days, after 14 days it falls sharply. Cells which undergo differentiation in vitro (e.g. HL-60 cells induced to differentiate with DMSO or TPA) down-regulate MCM3 but not Orc2 (Musahl, Aussois Meeting on DNA Replication, Aussois, France, June 1997). Differentiated cells from tissues ex vivo do not express MCM proteins such as MCM2 and MCM5. In co-pending patent application GB 9722217.8, it is shown that MCM5 is absent from differentiated cells of the uterine cervix and breast.

The six MCM proteins MCM2-MCM7 form a multiprotein complex, which splits into two subcomplexes: MCM3 and MCM5 dimer; MCM2-4-6-7 tetramer. MCM3 and MCM5 may be displaced from chromatin during S phase more slowly than MCM2-4-6-7 (Kubota et al., 1997, EMBO J. 16, 3320–3331). MCMs are chromatin-bound in G1, displaced during S phase, and nuclear, although not bound to chromatin, in G2.

In yeast and Xenopus assembly of the pre-RC is sequential with ORC recruiting Cdc6, which results in recruitment of MCM proteins (Coleman et al, 1996).

Human Cdc6 amino acid sequence is disclosed in Williams et al., 1997, *PNAS* USA 94: 142–147, GenBank Acc. No. U77949 and in WO 97/41153.

Human MCM2 sequence is disclosed in Todorov et al., 1994, *J. Cell Sci.*, 107, 253–265, GenBank Acc. No. X67334.

Human MCM3 sequence is disclosed in Thommes et al., 1992, *Nucl. Acid Res.*, 20, 1069–1074, GenBank Acc. No. P25205.

Human MCM4 sequence is disclosed in Ishimi et al., 1996, *J. Biol. Chem.*, 271, 24115–24122, GenBank Acc. No. X74794.

Human MCM5 sequence is disclosed in Hu et al., 1993, *Nucleic Acids Res.*, 21, 5289–5293, GenBank Acc. No. X74795.

Human MCM6 sequence is disclosed in Holthoff et al., 1996, *Genomics*, 37, 131–134, GenBank Acc. No. X67334.

Human MCM7 sequence is disclosed in Hu et al., 1993, *Nucleic Acids Res.*, 21, 5289–5293.

ATPase enzymatic activity has been reported for Cdc6 and for MCM proteins. (Zwerschke et al., 1994; Ishimi et al., 1997). These proteins may have other enzymatic activities, for instance helicase activity as reported by Ishimi et al., 1997.

Direct biochemical analysis of replication initiation in eukaryotic somatic cells has been impeded by the lack of an efficient mammalian cell-free DNA replication system to complement these cellular and genetic approaches.

We have previously developed a cell free system for initiating DNA replication under cell cycle control (Krude et al, 1997 and PCT/GB97/01751) in which there is provided:

(a) S phase cytosol or a fraction thereof in which are co-incubated (b) G1 phase nuclei, and (c) S phase nuclei or a fraction thereof and/or cyclins A and/or E complexed to their cognate cyclin dependent kinase (Cdk2).

DISCLOSURE OF THE INVENTION

Although our previous system allowed measurement of the initiation of DNA replication in vitro, preparations of G1 nuclei that are competent to replicate in that system are often contaminated with existing S phase nuclei. Hence we described various measures to identify these S phase contaminants such as BrdU labeling in vivo, and control incubations in G1 cytosol or dimethylaminopurine (DMAP). These measures work well for G1 nuclear populations with low levels of S phase contaminants, but are less satisfactory for preparations with high levels of S phase contaminants because the noise level rises relative to the initiation signal.

We have now refined this system and surprisingly found that by altering the method of preparation of G1 nuclei it is possible to dispense with the need for component (c) of the above system, and to improve the signal to noise ratio.

In particular, whereas we previously chemically induced is synchrony using a thymidine block and mitotic arrest by nocodazole, we found that the system may be improved using natural synchrony obtained by allowing untransformed cells to arrest growth in G0, and using such cells for the preparation of G1 nuclei.

In the examples which follow, we have used either mouse NIH 3T3 cells which show rigorous contact inhibition or human EJ30 cells which arrest in low serum. Release from contact inhibition is followed by entry into S-phase approximately 20 hours later for both NIH 3T3 and EJ30 cells, compared to about a 9 hour total G1 phase after release of HeLa cells from mitosis. We have used cells at various times after release from G0 as sources of G1 nuclei. This results in a high proportion of G1 nuclei that are competent to initiate in vitro as well as a lower frequency of S phase contaminants and hence a lower background noise. In addition, this protocol results in a simplified system that requires only competent G1 nuclei, S phase cytosol, deoxynucleoside triphosphates and an energy regenerating system to allow initiation of replication in vitro.

According to one aspect of the present invention there is provided a cell-free system for initiating DNA replication under cell cycle control, which system comprises:

a synchronous population of G1 nuclei which have been released from G0; and

S phase cytosol.

In a further aspect of the invention, there is provided a method for preparing G1 nuclei suitable for use in a cell-free system for initiating DNA synthesis which method comprises;

preparing a population of quiescent cells;

releasing said cells from quiescence;

cultivating said cells; and harvesting the nuclei of said cells prior to the end of G1.

Furthermore the invention also extends to G1 nuclei obtainable by such a method and to the use of such nuclei in a cell-free DNA replication system, either of the invention or of the prior art.

Furthermore, the invention provides a method for conducting a cell-free DNA replication assay which comprises:

providing a synchronous population of G1 nuclei obtained from cells which have been released from G0; and bringing said nuclei into contact with S phase cytosol under conditions suitable for DNA replication to occur.

Although not essential to the invention, the systems and assay may include one or more cyclin dependent kinases and/or their cognate cyclin components, including for example cyclin A and cyclin E both complexed to Cdk2, or a cyclin D complexed to Cdk 2, Cdk 4 or Cdk 6.

Furthermore, the present invention further provides the use of the cell free system disclosed above for identifying or obtaining an agent which modulates, e.g. inhibits or stimulates, DNA replication.

Such an agent may be identified by an assay method which comprises:

(a) treating a cell-free system according to the invention with a test substance; and (b) determining DNA synthesis.

Substances identified by such a method may be modified to produce analogues with improved activity.

Substances including modified substances identified according to the invention may be formulated into a composition including at least one additional component, such as a pharmaceutically acceptable excipient.

Using the cell free DNA replication system of the invention the inventors have further investigated the molecular mechanisms following release from quiescence that establish a replication-competent state during G1. It is shown that quiescent cells lack Cdc6 and that MCM proteins in these cells are not associated with chromatin. It is shown that on release from quiescence, competence to replicate coincides with expression of Cdc6 and the binding of the MCM protein complex to chromatin. Furthermore it is shown that addition of Cdc6 to G1 phase nuclei accelerates G1 progression causing premature entry into S phase and increases the proportion of nuclei replicating, thus further enhancing the signal to noise ratio of the system. Furthermore, the results suggest that addition of MCM protein will increase MCM binding to chromatin and promote premature initiation of DNA replication.

Therefore according to a further aspect of the present invention, there is provided a cell-free system for initiating DNA replication under cell cycle control, which system comprises:

a synchronous population of G1 nuclei which have been released from G0;

S phase cytosol; and a polypeptide supplied to the system;

wherein the said polypeptide is Cdc6 and/or at least one MCM protein.

In the context of the present application MCM protein is to be understood to refer to an MCM which might be or is selected from the group MCM2, MCM3, MCM4, MCM5, MCM6, MCM7. McM protein used may be mammalian such as human MCM protein or mouse MCM protein, amphibian such as Xenopus MCM protein or other eukaryotic such as *Saccharomyces cerevisiae* MCM protein and others as listed in Chong et al., 1996.

In the context of the present application, "being supplied" does not mean that the the Cdc6 is necessarily obtained from other cell types but that the Cdc6 in the system is present at a higher concentration than would occur in the template nuclei at the time of isolation under natural conditions prior to initiation of DNA replication. All references to the polypeptide supplied should be construed accordingly.

In a further aspect of the invention, there is provided a method of bringing forward initiation of DNA replication under cell cycle control in a cell-free system by supplying Cdc6 and/or at least one MCM protein to the system.

In another aspect of the present invention, there is provided a method for preparing G1 nuclei suitable for use in a cell-free system for initiating DNA synthesis which method comprises;

preparing a population of quiescent cells;

releasing said cells from quiescence;

cultivating said cells;

harvesting the nuclei of said cells prior to the end of G1;

and bringing said nuclei into contact with Cdc6 and/or at least one MCM protein supplied to the system.

Furthermore the invention also extends to G1 nuclei obtainable by such a method and to the use of such nuclei in a cell-free DNA replication system, either of the present invention or of the prior art.

Furthermore, it provides a method for conducting a cell-free DNA replication assay which comprises:

providing a synchronous population of G1 nuclei obtained from cells which have been released from G0;

bringing said nuclei into contact with S phase cytosol and Cdc6 and/or at least one MCM protein supplied to the assay under conditions suitable for DNA replication to occur.

Furthermore, it provides a method for promoting binding of MCM to chromatin in G1 stage nuclei which comprises bringing said nuclei into contact with supplied Cdc6.

It is shown that the ability of the G1 phase nuclei to prematurely become competent to replicate is dependent on the permeable state of the nuclear envelope. Bringing forward of the nuclei to competence can only be achieved if the G1 phase nuclei are made permeable.

Therefore, in yet further embodiments, the invention extends to G1 nuclei, cell-free systems, methods and assays and their use in which the G1 nuclei are permeabilised.

The S phase cytosol used in the cell-free systems according to the invention is generally supplemented with nucleoside and deoxynucleoside triphosphates (NTPs and dNTPs respectively). Usually, one of the deoxynucleoside triphosphates will be labeled.

BRIEF DESCRIPTION OF THE FIGURES

FIG. 4. DNA synthesis by G1 phase nuclei when incubated with S phase cytosol in the presence and absence of XCdc6.

FIG. 5. Average intensity of fluorescent labeling of XCdc6 performed on 80 impermeable nuclei and 80 permeabilised nuclei from both early and late time points.

DETAILED DESCRIPTION OF THE INVENTION

Figure 1:
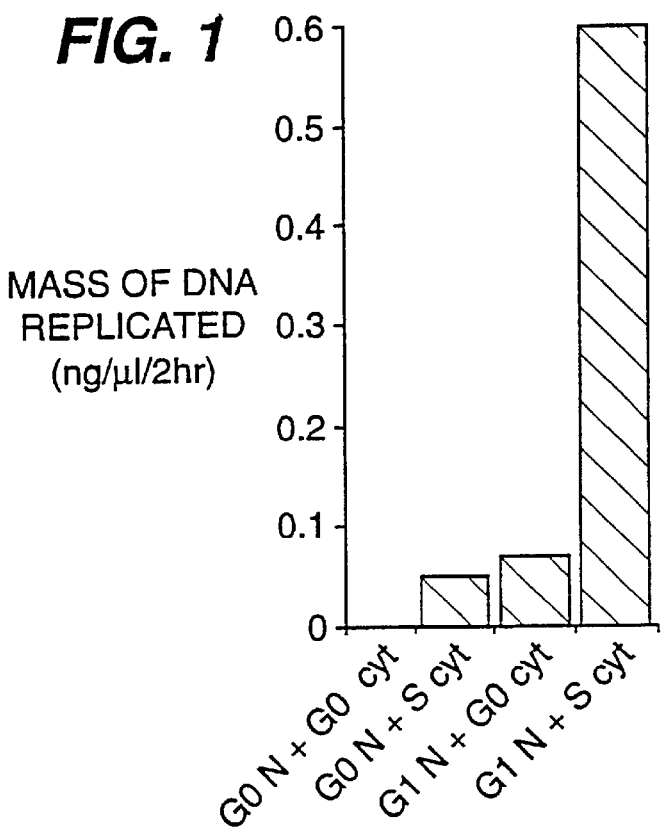
FIG. 1. DNA synthesis by G0 phase and G1 phase 3T3 nuclei when incubated in HeLa G0 phase and S phase cytosol.

The G1 nuclei of the present invention may be obtained from any mammalian cell, although human cells are preferred. The cells may be primary cell lines or transformed cell lines. Examples of primary cell lines include fibroblast, liver, and fetal cells. Transformed cell lines are widely available in the art and include tumour cell lines derived from bladder (such as the EJ30 cells illustrated in the examples), the cervix (such as HeLa cells), ovaries, liver, skin, muscle, nerves and white blood cells.

To prepare G1 nuclei in accordance with the present invention, cells are first of all cultured under conditions which induce quiescence. Cell culture conditions are well known per se in the art and reference may be made to the literature or the catalogues of commercial suppliers of culture medium for suitable conditions. Methods to induce quiescence and entry into G0 include serum starvation (e.g. cultivation with in media comprising less that 1%, for example about 0.5% serum), contact inhibition and isoleucine deprivation. Cells which are in G0 are then induced to enter G1 by for example adding serum (for example about 10%), replating at lower densities, or supplementing media with isoleucine. Cells are then cultivated for a period of time such that their nuclei, when isolated, are competent to enter S phase when stimulated with S phase cytosol.

Although the present invention primarily contemplates collecting nuclei in the G1 phase entered into immediately following release from G0, in principle the cells will remain substantially synchronous for at least one or two subsequent rounds of replication, and G1 nuclei may be collected during such subsequent rounds.

We have found that if nuclei are prepared from cells too early in G1 following release from G0, they are not competent to enter G1 in the presence of S phase cytosol. In 3T3 cells we have found that this transition to competence—which is prior to the actual entry to S phase—occurs at around 16 to 18 hours after release from G0. With the addition of exogenous Cdc6 to the S phase cytosol, we have found that this transition to competence occurs at around 15 hours after release from G0. For other cells the precise timing of the transition, where it occurs in the first place, may be determined by routine trial and error, for example by harvesting nuclei at a range of times post-release and determining the degree to which S phase cytosol induces-entry to S phase and by determining the degree to which the presence of exogenous Cdc6 brings forward the entry to S phase.

G1 nuclei may be harvested and stored frozen prior to use. Suitable conditions include equilibrating the nuclei in an equal volume of a buffer comprising 3% bovine serum albumin, 0.25M sucrose, 75 mM NaCl, 0.5 mM spermidine and 0.15 mM spermine.

In certain aspects of the invention, the nuclei are permeabilised. Nuclei may be permeabilised by physical methods such as Dounce homogenisation (Heintz and Stillman, 1988; Krude et al., 1997), chemical methods such as treatment with permeabilisation agents or by a combination of the two, such as Dounce homogenisation followed by treatment with a permeabilisation agent. Other physical methods include electroporation and sonication. A suitable permeabilisation agent is lysolecithin. When used in the examples of the present invention, lysolecithin was used at a stock concentration of 2 mg/ml and added in multiple 50 μl aliquots to 500 μl of nuclear suspension until nuclei became permeable to fluorescein-linked dextran (70 kDa). However, the precise amounts of lysolecithin used may be selected by those of skill in the art based upon the particular conditions and thus the values of such amounts are not essential to the present invention. The amounts may vary. In a typical preparation, the final volume of lysolecithin used may vary from 50 μL to 500 μl. However these figures are by way of guidance only and may be varied by those of skill in the art. Other permeabilisation agents include Nonidet NP-40, Triton e.g. Triton X100, digitonin, Streptolysin O, phospholipase A and melittin.

S phase cytosol may be obtained from any suitable population of synchronously replicating cells, in accordance with the methods described herein and by reference to the literature. S phase cytosol may be from any suitable source, including those primary and transformed cells as mentioned above. A preferred source of cytosol is the HeLa cytosol as described in the accompanying examples.

The precise amounts of G1 nuclei and S phase cytosol used in the system of the invention may be selected by those of skill in the art based upon the particular assay format which is to be used, and thus the values of such amounts are not essential to the present invention. The amounts may vary between large margins. In a typical assay, between from $10^3$ to $10^8$ G1 nuclei, for example from $10^5$ to $10^7$ nuclei may be used, together with S phase cytosol collected from say 100 times fewer to 100 times more, preferably from 10 times fewer to 10 times more, cells. However these figures are by way of guidance only and may be varied by those of skill in the art.

In particular examples of the system of the present invention, Xenopus Cdc6 (XCdc6) was used. However, Cdc6 which may be used in the system of the present invention is not limited to Xenopus Cdc6. Cdc6 proteins from any appropriate species e.g. mammalian such as human Cdc6, amphibian such as Xenopus Cdc6 or other eukaryotic such as *Saccharomyces cerevisiae* Cdc6. Furthermore, Cdc18, e.g. human Cdc18 or *Schizosaccharomyces pombe* Cdc18, which is homologous to Cdc6 may be used. Human Cdc6 amino acid sequence is disclosed in Williams et al., 1997, *PNAS* USA 94: 142–147, GenBank Acc. No. U77949 and in Wo 97/41153. Xenopus Cdc6 amino acid sequence is disclosed in Coleman et al., 1996, Cell 87 53–63, GenBank Acc. No. U66558 and in WO 97/41153. *Saccharomyces cerevisiae* Cdc6 amino acid sequence is disclosed in Bueno and Russell, 1992, EMBO J. 11 2167–2176, GenBank Acc. No. X65299. Human Cdc18 amino acid sequence is disclosed in Saha et al., GenBank Acc. No. AF022109. *Schizosaccharomyces pombe* Cdc18 amino acid sequence is disclosed in Kelly et al, 1993, Cell 74 371–382, GenBank Acc. No. LI6793.

Where applicable, instead of using a wild-type Cdc6 protein, an amino acid sequence variant, mutant, derivative, allele or homologue may be employed which preferably retains activity and characteristics of wild-type Cdc6 protein. Accordingly, Cdc6 to be used in the system of the invention is to be construed to include polypeptides which are encoded from nucleotide sequences which have a substantial identity with the nucleotide sequences which encode wild-type Cdc6 and which retain activity in the system of the present invention. Particularly preferred are Cdc6-like polypeptides encoded from nucleotide sequences which have greater than about 70%, preferably greater than about 80%, more preferably greater than about 85% or about 90% and most preferably greater than about 95% homology with nucleotide sequences encoding wild-type Cdc6 polypeptides of appropriate species, e.g. mammalian such as human Cdc6, amphibian such as Xenopus Cdc6 or other eukaryotic such as *Saccharomyces cerevisiae* Cdc6. The sequence may share greater than about 60% similarity, greater than about 70% similarity, greater than about 80% similarity or greater than about 90% similarity with the amino acid sequence. Amino acid similarity is generally defined with reference to the algorithm GAP (Genetics Computer Group, Madison, Wis.), or the TBLASTN program, of Altschul et al. (1990). Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Particular amino acid sequence variants may differ from from wild type sequences by insertion, addition, substitution or deletion of 1 amino acid, 2, 3, 4, 5–10, 10–20 20–30, 30–50, 50–100, 100–150, or more than 150 amino acids.

Sequence comparison may be made over the full-length of the relevant sequence, or may more preferably be over a contiguous sequence of about or greater than about 20, 25, 30, 33, 40, 50, 67, 133, 167, 200, 233, 267, 300, 333, 400, 450, 500 or more amino acids or nucleotide triplets, compared with the relevant amino acid sequence or nucleotide sequence as the case may be.

Cdc6-like polypeptides can be isolated by any means available to the skilled man. Cdc6 may be purified from natural sources or produced recombinantly. A convenient way of producing a Cdc6 polypeptide to be used in the system of the present invention is to express nucleic acid encoding it. This may conveniently be achieved by growing a host cell, containing a vector, under conditions which cause or allow expression of the polypeptide. Polypeptides may also be expressed in in vitro systems, such as reticulocyte lysate. Alleles, derivatives, variants and mutants may be expressed likewise. Systems for cloning and expression of a polypeptide in a variety of different host cells are well known. Suitable host cells include bacteria, eukaryotic cells such as mammalian cells and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is E. coli.

Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press. Transformation procedures depend on the host used, but are well known.

References to Cdc6 should be construed to encompass all molecules obtained as described above and which retain Cdc6-like activity i.e. promote premature initiation of DNA replication in the system of the present invention. They should further include the homologous protein Cdc18, found in, for example, *Schizosaccharomyces pombe.*

In the examples of the present invention, Xcdc6, when used, has been used at a concentration of 0.65 μM. However, the precise amounts of Cdc6 used in the system of the invention may be selected by those of skill in the art based upon the particular assay format and the type of Cdc6 which is to be used and thus the values of such amounts are not essential to the present invention. The amounts may vary between large margins. In a typical assay, the concentration of Cdc6 may vary from 0.065 μM to 6.50 μM. However these figures are by way of guidance only and may be varied by those of skill in the art.

The present invention extends to the use of MCM proteins in the system of the invention. Addition of MCM protein should increase MCM binding to chromatin and promote premature initiation of DNA replication. MCM protein used in the system of the invention may be mammalian such as human MCM protein or mouse MCM protein, amphibian such as Xenopus MCM protein or other eukaryotic such as *Saccharomyces cerevisiae* MCM protein. Any one of MCM2, MCM3, MCM4, MCM5, MCM6 or MCM7 can be used either in isolation or in combination. Human MCM2 sequence is disclosed in Todorov et al., 1994, *J. Cell Sci.*, 107, 253–265, GenBank Acc. No. X67334. Human MCM3 sequence is disclosed in Thommes et al., 1992, *Nucl. Acid Res.*, 20, 1069–1074, GenBank Acc. No. P25205. Human MCM4 sequence is disclosed in Ishimi et al., 1996, *J. Biol. Chem.*, 271, 24115–24122, GenBank Acc. No. X74794. Human MCMS sequence is disclosed in Hu et al., 1993, *Nucleic Acids Res.*, 21, 5289–5293, GenBank Acc. No. X74795. Human MCM6 sequence is disclosed in Holthoff et al., 1996, *Genomics*, 37, 131–134, GenBank-Acc. No. X67334. Human MCM7 sequence is disclosed in Hu et al., 1993, *Nucleic Acids Res.*, 21, 5289–5293. Alternative names of MCM family members together with references to the sequences are catalogued in Chong et al., 1996.

As with Cdc6 proteins, instead of using a wild-type MCM protein, an amino acid sequence variant, mutant, derivative, allele or homologue as defined for Cdc6 mutatis mutandis above may be employed which preferably retains activity and characteristics of wild-type MCM proteins.

The precise amounts of MCM used in the system of the invention may be selected by those of skill in the art based upon the particular assay format and the type of MCM which is to be used and thus the values of such amounts are not essential to the present invention. The amounts may vary between large margins. In a typical assay, the concentration of MCM may vary from 0.065 μM to 6.50 μM. However these figures are by way of guidance only and may be varied by those of skill in the art.

Also as mentioned above, the inclusion of one or more of cyclin A/cdk2, cyclin D/cdk2, cyclin D/cdk4, cyclin D/cdk6 and cyclin E/cdk2 is not excluded from the present invention. If one or more of the cyclin/cdk complexes are included, the preferred concentration of each complex may be about 0.1–1 μg/ml.

Where applicable, instead of using a wild-type cyclin A, D and/or cyclin E and Cdk2, 4 or 6, an amino acid sequence variant, mutant, derivative, allele or homologue may be employed which differs by one or more amino acid residues from the wild-type amino acid sequence, by one or more of addition, insertion, deletion and substitution of one or more amino acids. References to cyclins and their dependent kinases should be construed accordingly.

Methods of obtaining agents able to modulate DNA replication or initiation thereof include methods wherein a suitable end-point is used in the presence and absence of a test substance. Detailed disclosure in this respect is included below. It is worth noting, however, that combinatorial library technology provides an efficient way of testing a potentially vast number of different substances for ability to modulate activity. Such libraries and their use are known in the art, for all manner of natural products, small molecules and peptides, among others. The use of peptide libraries may be preferred in certain circumstances.

Appropriate agents may be obtained, designed and used for any of a variety of purposes.

Agents which inhibit DNA replication or synthesis or the initiation thereof may be used against cellular proliferative disorders, such as tumours/cancer, inflammation and psoriasis. They may be used for example in inducing apoptosis, in inhibiting cell replication, as anti-tumour or anti-inflammatory agents, and so on. Agents which stimulate DNA replication or synthesis or the initiation thereof may be used in any context where cellular stimulation is required or desirable, such as in promotion of angiogenesis, in healing of wounds, burns or tissue grafts. They may for example stimulate cell growth, cell regeneration, blood vessel formation, for instance in infarcted or compromised tissue, or in graft medication.

A test compound which disrupts, reduces, interferes with or wholly or partially abolishes DNA synthesis or replication may thus be identified. Likewise, a test compound which stimulates, increases, potentiates or augments DNA synthesis or replication may thus be identified.

DNA synthesis may be determined by any suitable means which may conveniently involve labelling of a deoxynucleoside and determining incorporation of the label into DNA. Any suitable label may be employed, including radioactivity and fluorescence. Scintillation counting or FACS analysis may conveniently be employed. In principle the amount of DNA being synthesised may be measured, but this would not be compatible with high through-put screening of test substances.

In one particular aspect of the invention, the proportion of nuclei replicating may be determined by staining all nuclei with a stain of a first colour and then incorporating a colourimetric label of a second colour into replicating DNA such that the label is detectable by light of a different wavelength to the first colour. By "colourimetric label" it is meant a label which is either coloured or capable of fluorescence in itself, or capable of being detected by a label which is coloured or capable of fluorescence.

In one embodiment of this aspect, we have used propidium iodide as the stain for all nuclei and biotinylated dUTP as the colourimetric label, which is detected with fluorescent streptavidin.

The assay result may be measured by low power field microscopy by observing the numbers of stained cells where replicating G1 nuclei are stained a different colour from non-replicating cells. Such a method lends itself to automation, since the different cells may be counted easily as different coloured points of light.

Performance of an assay method according to the present invention may be followed by isolation and/or manufacture and/or use of a compound, substance or molecule which tests positive for ability to modulate DNA synthesis.

The amount of test substance or compound which may be added to an assay of the invention will normally be determined by trial and error depending upon the type of compound used. Typically, from about 1 pM to 1 mM or more concentrations of putative inhibitor compound may be used, for example from 0.01 nM to 100 $\mu$M, e.g. 0.1 to 50 $\mu$M, such as about 10 $\mu$M. Greater concentrations may be used when a peptide is the test substance. Even a molecule with weak binding may be a useful lead compound for further investigation and development.

Compounds which may be used may be natural or synthetic chemical compounds used in drug screening programmes. Extracts of prokaryotes and/or eukaryotes, such as plants, which contain several characterised or uncharacterised components may also be used.

Antibodies and binding fragments thereof directed to one or more components of DNA replication apparatus or other cellular component form a further class of putative inhibitor compounds. Candidate inhibitor antibodies may be characterised and their binding regions determined to provide single chain antibodies and fragments thereof which are responsible for disrupting the interaction.

Other candidate inhibitor compounds may be based on modelling the 3-dimensional structure of a polypeptide or peptide fragment and using rational drug design to provide potential inhibitor compounds with particular molecular shape, size and charge characteristics.

A compound found to have the ability to affect DNA replication has therapeutic and other potential in a number of contexts, as discussed. For therapeutic treatment such a compound may be used in combination with any other active substance, e.g. for anti-tumour therapy another anti-tumour compound or therapy, such as radiotherapy or chemotherapy. Thus, the assay of the invention need not measure the degree of modulation, e.g inhibition or stimulation, of DNA synthesis caused by the compound being tested. Instead the effect on cell viability, cell killing (e.g. in the presence and absence of radio- and/or chemo-therapy) and so on, may be measured.

An agent identified using one or more primary screens as having ability to modulate DNA synthesis may be assessed further using one or more secondary screens. A secondary screen may involve testing for ability to enter a cell and be transported to the nucleus, and/or testing for ability to modulate cell replication.

Following identification of a substance or agent which modulates or affects DNA replication, the substance or agent may be investigated further. Furthermore, it may be manufactured and/or used in preparation, i.e. manufacture or formulation, of a composition such as a medicament, pharmaceutical composition or drug. These may be administered to individuals, e.g. for any of the purposes discussed elsewhere herein.

As noted, the agent may be peptidyl, e.g. a peptide which includes a sequence as recited above, or may be a functional analogue of such a peptide.

As used herein, the expression "functional analogue" relates to peptide variants or organic compounds having the same functional activity as a peptide in question. Examples of such analogues include chemical compounds which are modelled to resemble the three dimensional structure of a peptide or polypeptide domain, and in particular the arrangement of the key amino acid residues.

In a further aspect, the present invention provides the use of a substance identified or obtained using a cell-free system in accordance with the present invention in methods of designing or screening for mimetics of the substance.

Accordingly, the present invention provides a method of designing mimetics of a peptidyl substance able to modulate DNA replication identified or obtained using a cell-free system as disclosed, said method comprising:

(i) analysing the substance to determine the amino acid residues essential and important for the modulating activity to define a pharmacophore; and, (ii) modelling the pharmacophore to design and/or screen candidate mimetics having the modulating activity.

Suitable modelling techniques are known in the art. This includes the design of so-called "mimetics" which involves the study of the functional interactions fluorogenic oligonucleotide the molecules and the design of compounds which contain functional groups arranged in such a manner that they could reproduce those interactions.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are not well suited as active agents for oral compositions as they tend to be quickly degraded by proteases in the alimentary canal. Mimetic design, synthesis and testing may be used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

The mimetic or mimetics found by this approach can then be screened to see whether they have the target property, or to what extent they exhibit it. Further optimisation or modification can then be carried out to arrive at one or more final mimetics for in vivo or clinical testing.

Mimetics of this type together with their use in therapy form a further aspect of the invention.

Generally, such a substance, e.g. inhibitor or stimulator, according to the present invention is provided in an isolated and/or purified form, i.e. substantially pure. This may include being in a composition where it represents at least about 90% active ingredient, more preferably at least about 95%, more preferably at least about 98%. Such a composition may, however, include inert carrier materials or other pharmaceutically and physiologically acceptable excipients. As noted below, a composition according to the present invention may include in addition to an inhibitor compound as disclosed, one or more other molecules of therapeutic use, such as an anti-tumour agent.

The present invention extends in various aspects not only to a substance identified as a modulator of DNA replication, in accordance with what is disclosed herein, but also a pharmaceutical composition, medicament, drug or other composition comprising such a substance, a method comprising administration of such a composition to a patient, e.g. for a purpose discussed elsewhere herein, which may include preventative treatment, use of such a substance in manufacture of a composition for administration, e.g. for a purpose discussed elsewhere herein, and a method of making a pharmaceutical composition comprising admixing such a substance with a pharmaceutically acceptable excipient, vehicle or carrier, and optionally other ingredients.

A substance according to the present invention may be provided for use in a method of treatment of the human or animal body by therapy which affects DNA replication in cells, e.g. tumour cells. Other purposes of a method of treatment employing a substance in accordance with the present invention are discussed elsewhere herein.

Thus the invention further provides a method of modulating DNA replication, e.g. for a purpose discussed elsewhere herein, which includes administering an agent which modulates DNA replication or synthesis, such a method being useful in treatment where such modulation is desirable.

The invention further provides a method of treatment which includes administering to a patient an agent which modulates DNA replication or synthesis. Exemplary purposes of such treatment are discussed elsewhere herein.

Whether it is a polypeptide, antibody, peptide, nucleic acid molecule, small molecule, mimetic or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

A composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Liposomes, particularly cationic liposomes, may be used in carrier formulations.

Examples of techniques and protocols mentioned above can be found in Remington's Pharmaceutical Sciences, 16th edition, Osol, A. (ed), 1980.

The agent may be administered in a localised manner to a tumour site or other desired site or may be delivered in a manner in which it targets tumour or other cells.

Targeting therapies may be used to deliver the active agent more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

Instead of administering these agents directly, they may be produced in the target cells by expression from an encoding gene introduced into the cells, eg in a viral vector (a variant of the VDEPT technique—see below). The vector may targeted to the specific cells to be treated, or it may contain regulatory elements which are switched on more or less selectively by the target cells.

The agent (e.g. small molecule, mimetic) may be administered in a precursor form, for conversion to the active form by an activating agent produced in, or targeted to, the cells to be treated. This type of approach is sometimes known as ADEPT or VDEPT, the former involving targeting the activator to the cells by conjugation to a cell-specific antibody, while the latter involves producing the activator, e.g. an enzyme, in a vector by expression from encoding DNA in a viral vector (see for example, EP-A-415731 and WO 90/07936).

An agent may be administered in a form which is inactive but which is converted to an active form in the body. For instance, the agent may be phosphorylated (e.g. to improve solubility) with the phosphate being cleaved to provide an active form of the agent in the body.

A composition may be administered alone or in combination with other treatments, either simultaneously or sequentially dependent upon the condition to be treated, such as cancer or any other condition in which an effect on cell viability is desirable.

Nucleic acid according to the present invention, encoding a polypeptide or peptide able to modulate DNA replication, may be used in methods of gene therapy, for instance in treatment of individuals, e.g. with the aim of preventing or curing (wholly or partially) a disorder or for another purpose as discussed elsewhere herein.

Vectors such as viral vectors have been used in the prior art to introduce nucleic acid into a wide variety of different target cells. Typically the vectors are exposed to the target cells so that transfection can take place in a sufficient proportion of the cells to provide a useful therapeutic or prophylactic effect from the expression of the desired polypeptide. The transfected nucleic acid may be permanently incorporated into the genome of each of the targeted cells, providing long lasting effect, or alternatively the treatment may have to be repeated periodically.

A variety of vectors, both viral vectors and plasmid vectors, are known in the art, see U.S. Pat. No. 5,252,479 and WO 93/07282. In particular, a number of viruses have been used as gene transfer vectors, including papovaviruses, such as SV40, vaccinia virus, herpesviruses, including HSV and EBV, and retroviruses. Many gene therapy protocols in the prior art have used disabled murine retroviruses.

As an alternative to the use of viral vectors other known methods of introducing nucleic acid into cells includes electroporation, calcium phosphate co-precipitation, mechanical techniques such as microinjection, transfer mediated by liposomes and direct DNA uptake and receptor-mediated DNA transfer.

Receptor-mediated gene transfer, in which the nucleic acid is linked to a protein ligand via polylysine, with the ligand being specific for a receptor present on the surface of the target cells, is an example of a technique for specifically targeting nucleic acid to particular cells.

A polypeptide, peptide or other substance able to modulate or interfere with DNA replication or other substance as disclosed herein, or a nucleic acid molecule encoding a peptidyl such molecule, may be provided in a kit, e.g. sealed in a suitable container which protects its contents from the external environment. Such a kit may include instructions for use.

The following examples illustrate the invention.

EXAMPLE 1

S-phase Cytosol from HeLa Cells Induces DNA Replication in G1, but not G0 NIH 3T3 Nuclei in Vitro Nuclear templates were prepared by Dounce homogenisation as described previously, but from NIH 3T3 cells. G0, quiescent, cells were prepared by allowing NIH 3T3 cells to proliferate until they reached confluence and arrested their proliferation. They were released from quiescence by trypsinization and replating at ¼ the cell density. Cells were harvested as described previously (Krude et al., 1997) at measured times after release from quiescence. The 3T3 cells treated this way pass through G1 and begin to enter S phase synchronously about 21 hrs later. Nuclei and cytosolic extract were produced by hypotonically swelling the cells, scrape harvesting and Dounce-homogenizing. Nuclei were pelleted at 4500 rpm for 2 mins, washed once in SuNaSp/BSA (3% bovine serum albumin, 0.25M sucrose, 75 mM NaCl, 0.5 mM spermidine and 0.15 mM spermine). The cytosolic supernatant was respun at 14,000 rpm for 15 mins in an Eppendorf microfuge at 4° C. Nuclei can be stored frozen by equilibrating in an equal volume of SuNaSp/BSA. Cytosolic extracts from 3T3 cells were used fresh, unfrozen. Alternatively, cytosolic extracts can be snap frozen and stored in liquid $N_2$.

HeLa S phase extracts were prepared and incubated as described previously (Krude et al., 1997). Briefly, cells were thymidine-arrested at the G1/S border and released for 2 hours before harvesting as for 3T3 cytosol.

In vitro replication assays were performed in 50 μl reactions in 1.5 ml polypropylene tubes (Sarstedt or Eppendorf). Typically, 10 μl of a reaction buffer containing the labeling reagent (biotin-dUTP or $^{32}P$ dATP), unlabeled nucleoside triphosphates (NTP's) and deoxynucleoside triphosphates (dNTP's) and an energy regenerating system was added to 30 μl of cytosol and 5 μl of packed nuclei. The reaction was incubated at 37° C. for 3 hrs. Nuclei were fixed with formaldehyde (4% freshly prepared from paraformaldehyde in phosphate-buffered saline) and spun to polylysine-coated coverslips. Biotin-dUTP incorporation was detected by staining with fluorescein-streptavidin, whilst total DNA was visualized by propidium iodide. The samples were viewed by UV fluorescent or scanning laser confocal microscopy. The images were collected on a Bio-Rad MRC 1024 confocal microscope under identical conditions. In the images total DNA was red, biotin-dUTP incorporation was green, and so replicating nuclei appeared yellow. The percentage of nuclei replicating were calculated from many prints of confocal images.

Control incubations were performed with 3T3 G0 cytosol and in buffer A/BSA (1% bovine serum albumin, 60 mM KCl, 15 mM Tris HCl, 15 mM NaCl, 10 mM β-mercaptoethanol, 0.5 mM spermidine 0.15 mM spermine pH 7.4), both of which allow efficient elongation of S phase nuclei, but not initiation of replication by G1 nuclei. All control reactions were supplemented with the reaction buffer containing nucleoside and deoxynucleoside triphosphates as described in the third paragraph of this example above.

The percentage of yellow stained nuclei were found to be as follows:

TABLE 1

|  | Buffer A | G0 Cytosol | S Cytosol |
| --- | --- | --- | --- |
| 3T3 G1 nuclei | 4% | 10% | 52% |
| 3T3 G0 nuclei | <1% | <1% | <1% |
| 3T3 S nuclei | 64% | 64% | 89% |

Table 1 shows that nuclei from quiescent G0 NIH 3T3 cells fail to replicate in S phase cytosol, G0 cytosol or buffer A. In contrast G1 nuclei prepared 18 hours after release from quiescence initiate replication in S phase cytosol. They do not replicate in either G0 cytosol or buffer A confirming that they had not entered S phase already. The final row of Table 1 demonstrates that S phase nuclei can be recognised by their ability to elongate efficiently in G0 cytosol or buffer A, and that buffer A or G0 cytosol allow efficient elongation of S phase nuclei. Therefore, replication depends on S phase cytosol and a source of competent G1 nuclei. Unlike the previous version of the system described in PCT/GB97/01751, initiation of replication by G1 NIH 3T3 nuclei prepared in this way does not require S phase nuclei, or S phase nuclear extract or exogenous cyclin dependent kinases.

EXAMPLE 2

Nuclei Become Competent to Replicate at a Discrete Point in G1 Phase

The competence of G1 NIH 3T3 nuclei to replicate was determined by repeating the collection of G1 nuclei at different times following release from G0 arrest and incubating the nuclei with S phase cytosol in accordance with the procedures of Example 1. The results (percentage nuclei staining yellow) for the 16 and 18 hour time points, together with an S phase nuclei control, are summarized in Table 2 and show that competence arises suddenly between 16 h and 18 h after release from quiescence.

TABLE 2

|  | S cytosol | Buffer A |
| --- | --- | --- |
| G1 nuclei (16 hr) | 4% | <1% |
| G1 nuclei (18 hr) | 52% | 4% |
| S nuclei | 89% | 64% |

EXAMPLE 3

$^{32}$P DATP Incorporation Confirm that S Phase Cytosol Induces DNA Synthesis by G1 Nuclei Initiation of DNA replication can be quantitated biochemically by 32P incorporation. In vitro DNA replication reactions were performed using G0 and G1 Phase nuclei similarly to those in Example 1 but in the presence of $^{32}$P DATP. The reactions were incubated for 2 hours with two volumes of stop mix (1% SDS, 5 mM DTT, 1 mM EDTA, 50 mM Tris pH 6.8) added after the incubations. Aliquots were pipetted onto GFC filters in quadruplicate with two filters dried and used to measure total counts, whilst the other two filters were used TCA precipitated (10% TCA containing 2% NaPPi). The mass of DNA synthesised was calculated from the ratio of incorporated radiolabel to total available radiolabel in the incubation according to the formula ((TCA cpm/total cpm)×0.101=ng/µl DNA synthesised). FIG. 1 shows a comparison of $^{32}$P dATP incorporation obtained with G0 phase and G1 Phase 3T3 nuclei. G0 Phase nuclei failed to show significant amounts of DNA synthesis when incubated in HeLa S phase cytosol (0.4% of the genome synthesised). In contrast G1 Phase nuclei synthesised 5% of the genome when incubated in S phase cytosol.

EXAMPLE 4

$^{32}$P dATP Incorporation and Density Substitution Confirm that S Phase Cytosol Induces a Single Round of Semi-conservative DNA Synthesis by G1 Nuclei Buoyant CsCl density gradient centrifugation of DNA synthesised in 18-hour release G1 nuclei in the presence of BrdUTP and $^{32}$P dATP in S phase cytosol shows that the enhanced incorporation compared to the Buffer A control is semiconservative DNA synthesis.

To demonstrate this, in vitro incubations were performed similarly to those in Example 1, but in the presence of $^{32}$P dATP and BrdUTP. At the end of the incubation the samples were deproteinised by standard Proteinase K and Phenol:chloroform treatment, before buoyant CsCl gradient analysis. Fractions were collected and their refractive index was used to calculate density. Incorporated $^{32}$P DATP in each fraction was measured by TCA precipitation and liquid-scintillation counting.

Figure 2:
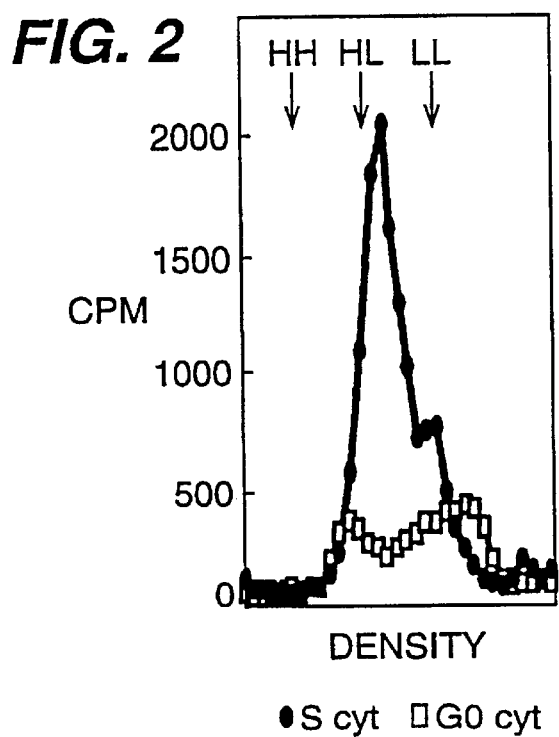
FIG. 2. $^{32}$P DATP incorporation measured against density of DNA synthesised by G1 nuclei in G0 phase and S phase cytosol.

The results are shown in FIG. 2. LL shows the position of unsubstituted parental DNA, HL of DNA fully substituted with BrdU in only one strand after one round of semiconservative replication and HH of DNA fully substituted in both strands after two rounds of replication. As is apparent, $^{32}$P DATP is combined with the dense thymidine analogue BrdUTP to show that S phase cytosol induces a single round of semi-conservative DNA replication in G1 nuclei. The validity of buffer A as the control incubation in FIG. 2 is clearly demonstrated for elongation of S phase nuclei in Tables 1 and 2.

EXAMPLE 5

Similar Results are Obtained with G1 Nuclei Prepared from EJ30/TG1 Human Cells Released from Quiescence In the previous examples we exploited 3T3 mouse cells as G0 or G1 templates because of their rigorous contact inhibition. We have also tested the value of quiescence for human cells using the human bladder cell line EJ30 clone TG1. These cells were driven into quiescence by serum starvation (0.5% serum) for 7 days and then released into G1 simply by feeding with normal, 10 serum, medium. Nuclei are harvested 12 hours after stimulation, and were prepared as 3T3 and HeLa nuclei, see Example 1 above. Nuclear extract was made as described in Krude et al, 1997.

It was found that HeLa S phase cytosol stimulated initiation of DNA replication in these G1 nuclei compared to the Buffer A control (about 31% vs about 21% yellow staining cells), but not in quiescent G0 nuclei. The background of S phase contaminants in the G1 nuclear preparation is higher for this cell line than for NIH 3T3. Nevertheless a strong stimulation by S phase cytosol was seen. Stimulation of initiation was slightly enhanced further in these G1 nuclei, but not in the G0 nuclei, by supplementing S cytosol with a nuclear extract from S phase HeLa cells (to about 35% yellow staining cells).

EXAMPLE 6

Competence of G1 Phase Nuclei to Replicate Coincides with Cdc6 Expression and Chromatin Binding of MCM Proteins in Vitro In Example 1, we have shown that S-phase cytosol from HeLa cells induces DNA replication in G1, but not G0 3T3 nuclei in vitro. In Example 2, we have shown that competence of G1 Phase nuclei to replicate arises suddenly between 16 h and 18 h after release from quiescence. To investigate why G0 nuclei or G1 Phase nuclei within 16 hours of release from quiescence fail to initiate DNA replication, we have investigated the presence and distribution of proteins of the pre-replicative complex, specifically Orc2, Mcm5 and Cdc6. Immunoblot studies were performed to look for changes in the abundance of these proteins as nuclei progress from an initiation-incompetent G0 to an initiation-competent state during G1.

Antibodies were raised to human Cdc6 Protein as follows. Several human expressed tags (ESTs) encoding a putative human homologue of Cdc6 were identified on the basis of their homology to yeast Cdc6/Cdc18 and human Orc1. Corresponding cDNA clones (110966, 204214, 294716; Image Consortium, Research Genetics Inc., USA) were sequenced by primer walking. Fragments corresponding to αα 145–360 and 364–547 were cloned into pET23a expression vector (Novagen) and expressed in *E.coli* CL41 strain (Miroux and Walker, 1996). The expressed proteins were purified by nickel affinity chromatography and used to immunise rabbits. Immunisation protocol and affinity purification of antibodies were performed as previously described (Romanowski et al., 1996a, 1996b). Antibodies to human Orc2 and Mcm5 proteins were raised and affinity purified as previously described (Romanowski et al., 1996a, 1996b).

For Western blot analysis, 3T3 cells were synchronised using the method described in Example 1 and total extracts were taken at 0 hours (G0) and at 3, 12, 18 hours (G1) and 21 hours (S) following quiescence, fractionated into soluble and chromatin-bound fractions (Heintz and Stillman, 1988), separated on SDS 12% polyacrylamide gels and immunoblotted with antibodies against hOrc2, hCdc6 and hMcm5. Blocking, antibody incubation and washing steps were performed in TBS/Tween-20 (1%)/Milk (10%). Immunoreactive bands were visualised on a preflashed Kodak XLS1 Scientific Imaging film by enhanced chemiluminescence (ECL, Amersham).

Figure 3:
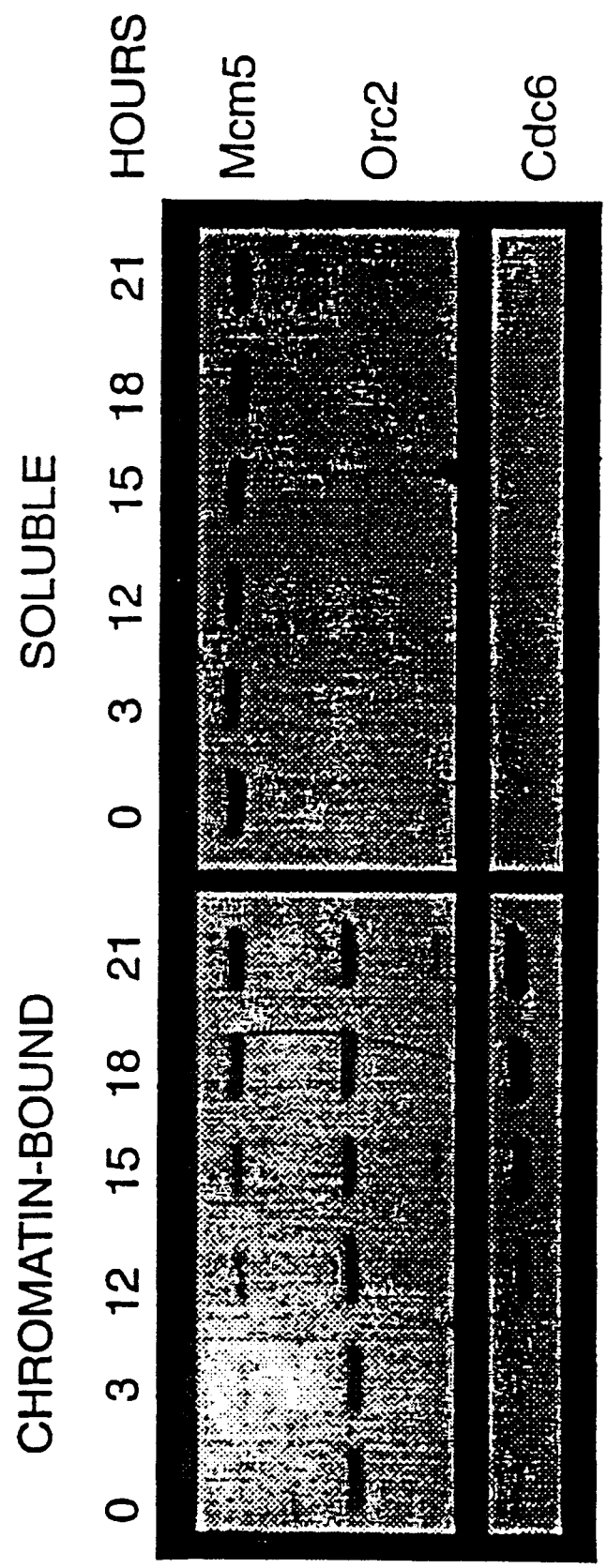
FIG. 3. Western Blots of chromatin-bound fractions and soluble fractions of total 3T3 cell extracts obtained at 0, 3, 12, 15, 18 and 21 hours following quiescence. Fractions were immunoblotted with antibodies against hOrc2, hCdc6 and hMcm5.

As shown in FIG. 3, Orc2 is exclusively present in the chromatin-bound fraction and its levels do not vary from G0 to S phase. In contrast Cdc6 is completely absent from quiescent cells but becomes detectable on chromatin 12 hours after release from quiescence. Consistent with this result from murine 3T3 cells, we have also found down-regulation of Cdc6 expression in quiescent human newborn fibroblasts and in the human carcinoma cell line EJ30 arrested by serum starvation (data not shown). The levels of soluble Mcm5 Protein do not vary significantly during the release. However, Mcm5 Protein is absent from the chromatin-bound fraction in quiescent cells and binds to chromatin 15–18 hours after release. The appearance of Mcm5 on chromatin follows that of Cdc6 and the levels of both proteins on chromatin reach saturation at about 18 hours after release from quiescence.

In Example 2, we have shown that competence of G1 Phase nuclei to replicate arises suddenly between 16 h and 18 h after release from quiescence. We have therefore demonstrated that G1 phase nuclei competence to initiate DNA replication arises at the time of maximal Cdc6 protein accumulation and chromatin binding of Mcm5. This suggests that the inability of G0 nuclei to replicate in the mammalian cell-free system might be due to the lack of Cdc6 and that competence to replicate in vitro following release from quiescence corresponds to the assembly of pre-replicative complexes from pre-existing ORC, newly synthesised Cdc6 and chromatin binding of MCM proteins in vivo.

The absence of Cdc6 in quiescence in contrast to its presence in the proliferative state suggests that Cdc6 may be used as a novel and powerful proliferation marker. Co-pending GB application 9722217.8 describes the use of antibodies against human Cdc6 and Mcm5 to identify pre-malignant cells and thus to improve the sensitivity of the standard Papanicolaou (PAP) cervical smear test. GB application 9722217.8 discloses that anti-cdc6 binding molecules are very effective in marking abnormality in various tissues, especially cervical samples, preferably smears. This compares with no binding to normal cervical tissue in a smear sample. Similarly it is shown that binding molecules directed against MCM5 are very effective in marking abnormality in various tissues, especially cervical samples, preferably smears. Thus, binding of (e.g.) an anti-Cdc6 or anti-MCM5 specific binding member to a sample provides for categorising the tissue from which the sample is derived as abnormal, potentially or actually pre-cancerous or cancerous, dysplastic or neoplastic.

EXAMPLE 7

Addition of Cdc6 Promotes Premature Initiation of DNA Replication in G1 Phase Nuclei G1 phase nuclei were prepared as described above and incubations as in Examples 1 and 2 were performed but in the presence of baculovirus expressed and nickel affinity purified His-tagged Xenopus Cdc6 (0.65 μM). In this particular example, Xenopus Cdc6 (XCdc6) was used. However, other Cdc6 proteins e.g. human Cdc6 may be used.

XCdc6 was expressed in Sf9 insect cells. Sf9 cells were grown in 400 ml Grace medium (Gibco BRL) containing FCS (5%), gentamycin (5 μg/ml) in spinners at 27° C. up to a density of $1.5 \times 10^6$ ml$^{-1}$. Cells were pelleted, resuspended in 50 ml medium containing recombinant baculovirus and incubated for 2 hours with gentle mixing. The culture was diluted to 400 ml with fresh medium and incubated for a further 48 hours. Cells were washed gently with ice-cold PBS and resuspended in 10 ml hypotonic buffer (HEPES pH 7.4 (10 mM), NaCl (10 mM), EGTA (1 mM), β-mercaptoethanol (1 mM), PMSF (1 mM), 10 μg/ml of each of leupeptin, aprotinin, pepstatin, chymostatin). Cells were allowed to swell for 10 min and lysed by passing through a tight fitting Dounce homogeniser.

Immediately, after lysis, NaCl concentration was restored to 150 mM. The lysate was spun at 5000 g for 10 min. The supernatant was then removed and spun again at 100000 g for 1 hour. The supernatant was removed and bound to 1 ml of Ni$^{2+}$-NTA agarose in a batch mode at 4° C. for 2 hours. A wash and three elution steps were performed at 4° C. with HEPES pH 7.4 (20 mM), NaCl (150 mM), EGTA (1 mM), glycerol (10%), β-mercaptoethanol (1 mM), PMSF (1 mM), 10 μg/ml of each of leupeptin, aprotinin, pepstatin, chymostatin containing 10 mM, 20 mM, 50 mM and 100 mM imidazole respectively. Protein containing fractions were pooled, dialysed against HEPES pH 7.5 (20 mM), NaCl (150 mM), glycerol (5%), DTT (1 mM) at 4° C. overnight, and concentrated using Vivaspin concentrators (Vivascience). The biochemical activity of nickel affinity purified His-tagged XCdc6 was tested by rescuing replication of exogenously added sperm chromatin in Cdc6-depleted Xenopus egg extract (Coleman et al., 1996).

The competence of G1 NIH 3T3 nuclei to replicate was determined by repeating the collection of G1 nuclei at 10 hours, 15 hours and 16.5 hours following release from G0 arrest and incubating the nuclei with S phase cytosol in accordance with the procedures of Example 2, but in the presence of His-tagged Xenopus Cdc6 (0.65 μM). The results (percentage nuclei staining yellow) for the time points, together with controls in which His-tagged Xenopus Cdc6 is absent, are summarized in Table 3 and show that addition of Cdc6 promotes premature initiation of DNA replication in G1 phase.

TABLE 3

|  | S cytosol | S cytosol + XCdc6 |
| --- | --- | --- |
| G1 nuclei (10 hr) | <1% | <1% |
| G1 nuclei (15 hr) | <1% | 82% |
| G1 nuclei (16.25 hr) | 38% | 78% |

Table 3 shows that no replication was detected for G1 phase nuclei prepared 10 hours after release from quiescence when incubated in HeLa S cytosol in the presence or absence of XCdc6. Similarly G1 phase nuclei prepared 15 hours after release from quiescence did not initiate replication in the presence of S cytosol. However, the addition of XCdc6 to the reaction resulted in 82% of the nuclei replicating. 38% of the G1 phase nuclei prepared 16.5 hours after release from quiescence initiated replication in the presence of S cytosol but in the absence of exogenous XCdc6. However, 78% of nuclei isolated at the same time but incubated in the presence of exogenous XCdc6 initiated replication.

Using the method described in Example 3 the amount of DNA synthesised in G1 phase nuclei in the presence or absence of XCdc6 was measured using nuclei prepared 16.25 hours after release from G0. A low background of DNA synthesis in these nuclei was observed when incubated in buffer A/BSA with NTPs and dNTPs representing S phase contaminants. The same nuclei synthesised approximately 4.9% of the genome when incubated in the presence of S phase cytosol (FIG. 4). However, XCdc6 stimulated DNA synthesis a further two-fold more than S phase cytosol alone (FIG. 4).

Using the method described in Example 4, BrdU substitution and buoyant density gradient centrifugation was used to examine whether addition of XCdc6 causes DNA re-replication. DNA synthesised in the presence of XCdc6 was predominantly hemisubstituted (HL) with BrdU indicating a single round of semiconservative replication. No DNA re-replication which would result in fully substituted DNA (HH) was detectable.

These results demonstrate that Cdc6 accelerates G1 Progression of 3T3 nuclei in vitro resulting in premature entry into S phase. Furthermore, the results show that not only does addition of exogenous Cdc6 protein cause premature initiation of replication but for nuclei prepared between 16 and 18 hours after release from quiescence, it also increases the proportion of nuclei replicating. Thus addition of exogenous Cdc6 protein can further increase the ratio of signal to background noise in the system. Furthermore the demonstrated effect of Cdc6 to induce replication in nuclei that are even further from the temporal border between the G1 and S stages reinforces our conclusion that the cell system of the present invention is inducing initiation of DNA replication and not just elongation of existing S phase contaminants.

EXAMPLE 8

Permeabilisation of the Nuclear Envelope Promotes Cdc6 Induced Premature Initiation of DNA Replication in G1 Phase Nuclei Nuclear preparation by Dounce homogenisation of hypotonically swollen cells as described above produced nuclei with variable nuclear permeability (0–60%) as shown by entry of dextran fluorescein by diffusion (data not shown). On addition to S phase cytosol many nuclei were observed to be transiently permeable but the nuclear membrane resealed within 15 minutes. The ability of exogenous XCdc6 to promote premature initiation of DNA replication was also found to vary between different batches of nuclei prepared by Dounce homogenisation.

The effect of nuclear membrane permeability on the response of nuclei to XCdc6 was investigated by selecting a preparation of 18 hour release G1 phase nuclei prepared by Dounce homogenisation which was shown to be impermeable to dextran fluorescein, dividing the preparation into two aliquots, fully permeabilising one aliquot and comparing the response of the permeabilised and impermeable nuclear preparations to exogenous XCdc6 (0.65 μM)

For permeabilisation, frozen 3T3 nuclei were resuspended in 500 μl SuNaSp (250 mM sucrose, 75 mM NaCl, 0.5 mM spermidine and 0.15 mM spermine), supplemented with 10 μg/ml leupeptin, pepstatin. A, and aprotinin, and spun down (2000 rpm in an Eppendorf 5415C centrifuge for 2 minutes at 4° C.). Nuclei were washed three times and resuspended in 500 μl SuNaSp. For permeabilisation 50 μl lysolecithin (2 mg/ml) was added and the nuclei were incubated on ice for 10 minutes. Permeability of the nuclear membrane after lysolecithin treatment was assessed by monitoring the extent of inclusion of fluorescein-linked dextran molecules (Molecular Probes) in nuclei stained with Hoechst 33258 (Sigma) (Coverley et al., 1993). (Fluorescein-linked dextran (70 KDa) lacks an NLS (nuclear localisation sequence) and is large enough to be retarded by an intact nuclear envelope). Nuclei were incubated with fluorescein-linked dextran and Hoechst 33258 and visualised by fluorescent confocal microscopy. Determination of the extent of nuclear membrane permeability was made after 2 min incubations with dye. The permeabilisation reaction was stopped by addition of 500 μl 3% BSA/SuNaSp. Nuclei were washed three times and resuspended in 20 μl 3% BSA/SuNaSp.

The response of permeabilised and impermeable aliquots to exogenous XCdc6 was compared using the in vitro cell free replication system. The results are summarised in Table 4 and show that Cdc6-induced premature initiation of DNA replication is promoted by permeabilisation of nuclear envelopes.

TABLE 4

|  | S cytosol | S cytosol + XCdc6 |
| --- | --- | --- |
| Impermeable | 41% | 40% |
| Permeable | 40% | 65% |

Table 4 shows that impermeable GI nuclei failed to respond to exogenous XCdc6. In contrast 65% of the lysolecithin-treated (Permeabilised) G1 nuclei were observed to replicate compared to 40% in its absence. The DNA replication signal in G1 nuclei incubated in S cytosol alone was not influenced by the permeabilisation of the nuclear envelope with lysolecithin, excluding the possibility that the increased signal is due to permeabilisation alone.

To confirm that permeabilising the nuclear envelope allows the binding of exogenous XCdc6 to chromatin, nuclear localisation of His-tagged XCdc6 was determined for both permeabilised and impermeable G1 phase nuclei prepared 18 hours after release from quiescence using a monoclonal anti His-tag antibody (Qiagen) at both 15 minutes and 3 hours after incubation in Hela S phase cytosol with XCdc6. Nuclei were spun through a 30% sucrose gradient onto coverslips, and stained for the presence of His-tagged XCdc6 with monoclonal anti His-tag antibody and for the presence of DNA with TOTO-3 (Molecular Probes). Nuclear localisation of XCdc6 was analysed by confocal fluorescence microscopy and the intensity of fluorescent labeling was measured using the LASERSHARP (Biorad) processing programme.

FIG. 5 shows the average intensity of fluorescent labeling of XCdc6 performed on 80 impermeable nuclei and 80 permeabilised nuclei from both early and late time points. Permeabilised nuclei showed an eleven-fold increase in the intensity of Xcdc6 fluorescence staining compared with impermeable nuclei after 3 hour incubation in HeLa S cytosol. Even after only 15 minutes, a two-fold difference was identified.

These results clearly show that nuclear envelope permeabilisation stimulates Cdc6 binding and that Cdc6 stimulates DNA replication only when the nuclear envelope is permeabilised.

EXAMPLE 9

Inhibitors of Protein Kinases Exemplify the Use of the Cell Free System to Assay for Compounds that Inhibit DNA Replication An assay according to the present invention was performed using two different CDK inhibitors, roscovitin and olomoucine. Roscovitin was a gift from L. Meijer, and was as described in Meijer, 1996. Olomoucine was purchased from Sigma Chemical Co., Poole, Dorset UK (http://www.sigma.sial.com). Although the assay system of the present invention does not require CDKs to be provided exogenously, inhibition by roscovitin and olomoucine suggest that cyclin/CDKS are present in nuclei prepared in the way described here.

3T3 nuclei were prepared and incubated with HeLa S phase cytosol in accordance with Example 1 above, and in addition further experiments were run in which various concentrations of roscovitin and olomoucine were added.

In the absence of these inhibitors, about 50% of yellow staining nuclei were seen, as before. Both 1 μM and 1 mM of roscovitin resulted in about a 5-fold decrease, and a similar decrease was observed with 2 mM of olomoucine. The decrease was less, to about 18%, with 10 μM of this inhibitor.

The following documents, mentioned above, are hereby incorporated by reference:
Altschul et al. (1990) J. Mol. Biol. 215 403–10
Aparicio et al. (1997) Cell 91 59–69
Bell and Stillman (1992) Nature 357 128–134
Bueno and Russell (1992) EMBO J. 11 2167–2176
Carpenter et al. (1996) Nature 379 357–360
Chong et al. (1995) Nature 375 418–421
Chong et al. (1996) Trends Biochem. Sci. 21 102–106
Cocker et al. (1996) Nature 379 180–182
Coleman et al. (1996) Cell 87 53–63
Coué et al. (1996) EMBO J. 15 1085–1097
Coverley et al. (1993) J. Cell Biol. 122 985–992
Dalton andd Whitbread (1995) P.N.A.S. 92 2514–2518
de Terra (1967) P.N.A.S. 57 607–614.
Detweiler and Li (1997) J. Cell Sci. 110 753–763
Detweiler and Li (1998) P.N.A.S. 95 2384–2389
Diffley and Cocker (1992) Nature 357 169–172
Diffley et al. (1994) Cell 78 303–316
Donovan and Diffley (1996) Curr. Opin. Genet. Dev. 6 203–207
Dutta and Bell (1997) Annu. Rev. Cell Dev. Biol. 13 293–332
Gavin et al. (1995) Science 270 16667–1671
Graham et al. (1966) Dev. Biol. 14 349–381.
Guttes and Guttes (1968)J. Cell Biol. 37 761–772.
Harris et al. (1966). J. Cell Sci. 1 1–30.
Heichman and Roberts (1994) Cell 79 557–562.
Heintz and Stillman (1988) Mol. Cell Biol. 8 1923–1931
Hendrickson et al. (1996) P.N.A.S. 93 12223–12228
Holthoff et al. (1996) Genomics 37, 131–134
Hu et al. (1993) Nucleic Acids Res. 21 5289–5293.
Ishimi et al. (1996) J. Biol. Chem. 271 24115–24122
Ishimi et al. (1997) J. Biol. Chem. 272 24508–24513
Johnson and Harris (1969) J. Cell Sci. 5 625–643.
Kelly et al. (1993) Cell 74 371–382
Kimura et al. (1994) EMBO J. 13 4311–4320
Krude et al. (1996) J. Cell Sci. 109 309–318
Krude, Jackman, Pines and Laskey (1997) Cell 88 109–119
Kubota et al. (1995) Cell 81 601–609
Kubota et al. (1997) EMBO J. 16 3320–3331
Liang et al. (1995) Cell 81 667–676
Liang and Stillman (1997) Genes and Dev. 11 3375–3386
Madine et al. (1995a) Nature 375 421–424
Madine et al. (1995b) Curr. Biol. 5 1270–1279
Meijer (1996) Trends in Cell Biol. 6 393–397.
Miroux and Walker (1996) Nature 367 236–242
Muzi-Falconi et al. (1996) P.N.A.S. 93 1566–1570
Newlon (1997) Cell 91 717–720
Nishitani and Nurse (1995) Cell 83 397–40
Nurse (1994) Cell 79 547–550.
Ord (1969) Nature 221 964–966
Piatti et al. (1995) EMBO J. 14 3788–3799
Rao and Johnson (1970) Nature 225 159–164.
Romanowski et al. (1996a) Curr. Biol. 6 1416–1425
Romanowski et al. (1996b) P.N.A.S. 93 10189–10194
Romanowski and Madine (1996) Trends Cell Biol. 6 184–188.
Rowles et al. (1996) Cell 87 287–296
Stillman (1996) Science 274 1659–1664
Tanaka et al. (1997) Cell 90 649–660
Thommes et al. (1992) Nucl. Acid Res. 20 1069–1074
Todorov et al. (1994) J. Cell Sci. 107 253–265
Todorov et al. (1995) J. Cell Biol. 129 1433–1455
Williams et al. (1997) PNAS USA 94 142–147
Yan et al. (1998) J. Biol. Chem. 269 23351–23356
Zwerschke et al. (1994) J. Biol. Chem. 269, 23351–23356

What is claimed is:

1. A method for conducting a cell-free assay for the initiation of DNA replication which comprises:

providing a synchronous population of G1 nuclei obtained from non-transformed cell lines which have been released from G0;

bringing said nuclei into contact with somatic cell S phase cytosol under conditions suitable for DNA replication to occur;

incubating a test substance with said nuclei and cytosol; and determining whether or not initiation of DNA replication occurs in the presence of said test substance.

2. The method of claim 1 which comprises supplying to the S phase cytocol at least one protein selected from cdc6 and an MCM protein.

3. The method of claim 2, further including permeabilising the harvested nuclei prior to bringing said nuclei into contact with Cdc6 and/or at least one MCM protein.

4. A method according to claim 1, wherein the substance is an inhibitor of DNA synthesis.

5. A method according to claim 1, wherein the substance is a stimulator of DNA synthesis.

6. The method of claim 1 wherein when said test substance is identified as an agent which modulates DNA replication, said test substance is modified.

7. The method of claim 6 wherein said test substance is modelled according to its physical properties including at least one physical property selected form the group of stereochemistry, bonding, size and charge, or said test substance is modelled by computational analysis.

8. A method according to claim 6 wherein the substance is modified to alter a property of the substance.

9. A method according to claim 8 wherein the substance is modified to alter its ability to modulate initiation of DNA replication.

10. A method of claim 1 wherein when said test substance is identified as an agent which modulates DNA replication, said test substance is formulated into a composition including at least one additional component.

11. A method according to claim 10 wherein the composition includes a pharmaceutically acceptable excipient.

* * * * *